(12) United States Patent
Amplatz et al.

(10) Patent No.: US 12,114,844 B2
(45) Date of Patent: Oct. 15, 2024

(54) PERCUTANEOUS CATHETER DIRECTED INTRAVASCULAR OCCLUSION DEVICES

(71) Applicant: St. Jude Medical, Cardiology Division, Inc., St. Paul, MN (US)

(72) Inventors: Kurt Amplatz, North Oaks, MN (US); Xiaoping Gu, Plymouth, MN (US); John C. Oslund, Blaine, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 407 days.

(21) Appl. No.: 17/407,736

(22) Filed: Aug. 20, 2021

(65) Prior Publication Data

US 2021/0378645 A1    Dec. 9, 2021

Related U.S. Application Data

(60) Continuation of application No. 16/179,503, filed on Nov. 2, 2018, now Pat. No. 11,116,486, which is a
(Continued)

(51) Int. Cl.
*A61B 17/00* (2006.01)
*A61B 17/12* (2006.01)

(52) U.S. Cl.
CPC .... *A61B 17/0057* (2013.01); *A61B 17/12022* (2013.01); *A61B 17/12109* (2013.01);
(Continued)

(58) Field of Classification Search
CPC .......... A61B 17/0057; A61B 17/12022; A61B 17/12109; A61B 17/12122;
(Continued)

(56) References Cited

U.S. PATENT DOCUMENTS

| 3,874,388 A | 4/1975 | King et al. |
| 4,007,743 A | 2/1977 | Blake |

(Continued)

FOREIGN PATENT DOCUMENTS

| AU | 489252 B | 10/1976 |
| CA | 2302164 A1 | 3/1999 |

(Continued)

OTHER PUBLICATIONS

"Catheter Closure of the Dustus Arteriosus" by Lee Benson, from pp. 321-333 Transcatheter Therapy in Pediatric Cardiology—1993.
(Continued)

*Primary Examiner* — Richard G Louis
(74) *Attorney, Agent, or Firm* — Armstrong Teasdale LLP

(57) ABSTRACT

A collapsible medical device and methods for deploying the same are provided. The medical device includes a tubular metal fabric, which includes a plurality of braided metal strands and a proximal end and a distal end, the tubular metal fabric having a collapsed configuration for delivery and an expanded preset configuration for creating an occlusion of an opening. In the expanded preset configuration, the device has two expanded disk portions and a central portion, a first expanded disk portion and the central portion connected by a first reduced diameter portion, and a second expanded disk portion and the central portion connected by a second reduced diameter portion. Each of the first and second reduced diameter portions is smaller in diameter than both the two expanded disk portions and the central portion, and each of the first and second reduced diameter portions is recessed into the central portion.

19 Claims, 12 Drawing Sheets

Related U.S. Application Data continuation of application No. 14/593,039, filed on Jan. 9, 2015, now Pat. No. 10,149,669, which is a continuation of application No. 13/837,351, filed on Mar. 15, 2013, now Pat. No. 8,961,556, which is a continuation of application No. 13/216,784, filed on Aug. 24, 2011, now Pat. No. 8,454,633, which is a division of application No. 11/827,590, filed on Jul. 12, 2007, now Pat. No. 8,034,061.

(52) U.S. Cl.
CPC .. *A61B 17/12122* (2013.01); *A61B 17/12172* (2013.01); *A61B 17/12177* (2013.01); *A61B 2017/00575* (2013.01); *A61B 2017/00592* (2013.01); *A61B 2017/00606* (2013.01); *A61B 2017/00628* (2013.01); *A61B 2017/00632* (2013.01); *A61B 2017/00867* (2013.01)

(58) Field of Classification Search
CPC ........ A61B 17/12172; A61B 17/12177; A61B 2017/00575; A61B 2017/00592; A61B 2017/00606; A61B 2017/00628; A61B 2017/00632; A61B 2017/00867; A61B 17/00; A61B 17/08; A61F 2/00; A61M 25/01

See application file for complete search history.

(56) References Cited

U.S. PATENT DOCUMENTS

| | | | |
|---|---|---|---|
| 4,619,246 A | 10/1986 | Molgaard et al. | |
| 4,836,204 A | 6/1989 | Landymore et al. | |
| 4,917,089 A | 4/1990 | Sideris | |
| 4,921,484 A | 5/1990 | Hillstead | |
| 4,991,602 A | 2/1991 | Amplatz et al. | |
| 5,064,435 A | 11/1991 | Porter | |
| 5,067,489 A | 11/1991 | Lind | |
| 5,108,420 A | 4/1992 | Marks | |
| 5,171,259 A | 12/1992 | Inoue | |
| 5,334,217 A | 8/1994 | Das | |
| 5,451,235 A | 9/1995 | Lock et al. | |
| 5,456,693 A | 10/1995 | Conston et al. | |
| 5,466,242 A | 11/1995 | Mori | |
| 5,522,822 A | 6/1996 | Phelps et al. | |
| 5,725,552 A | 3/1998 | Kotula et al. | |
| 5,846,216 A * | 12/1998 | Gonzales | A61M 31/00 604/514 |
| 5,846,261 A * | 12/1998 | Kotula | A61B 17/12122 606/213 |
| 5,944,738 A | 8/1999 | Amplatz et al. | |
| 6,080,182 A | 6/2000 | Shaw et al. | |
| 6,123,715 A | 9/2000 | Amplatz | |
| 6,168,622 B1 | 1/2001 | Mazzocchi | |
| 6,214,029 B1 | 4/2001 | Thill et al. | |
| 6,368,339 B1 | 4/2002 | Amplatz | |
| 6,447,531 B1 | 9/2002 | Amplatz | |
| 6,506,204 B2 | 1/2003 | Mazzocchi | |
| 6,551,344 B2 | 4/2003 | Thill | |
| 6,599,308 B2 | 7/2003 | Amplatz | |
| 6,682,546 B2 | 1/2004 | Amplatz | |
| 6,991,037 B2 | 1/2006 | Hocking | |
| 7,001,409 B2 | 2/2006 | Amplatz | |
| 7,195,636 B2 | 3/2007 | Avellanet et al. | |
| 7,665,466 B2 | 2/2010 | Figulla et al. | |
| 8,034,061 B2 | 10/2011 | Amplatz et al. | |
| 8,454,633 B2 | 6/2013 | Amplatz et al. | |
| 2002/0143349 A1 | 10/2002 | Gifford, III et al. | |
| 2003/0057156 A1 | 3/2003 | Peterson et al. | |
| 2004/0127935 A1 | 7/2004 | VanTassel et al. | |
| 2004/0143293 A1 | 7/2004 | Marino et al. | |
| 2007/0066993 A1 | 3/2007 | Kreidler | |
| 2007/0083230 A1 | 4/2007 | Javois | |
| 2007/0167980 A1 | 7/2007 | Figulla et al. | |
| 2007/0265656 A1 * | 11/2007 | Amplatz | A61B 17/12122 606/200 |
| 2008/0051830 A1 | 2/2008 | Eidenschink et al. | |

FOREIGN PATENT DOCUMENTS

| | | |
|---|---|---|
| CA | 2319521 A1 | 8/1999 |
| CA | 2402101 A1 | 10/2001 |
| CA | 2302164 C | 3/2004 |
| CA | 2319521 C | 5/2004 |
| CA | 2549323 A1 | 10/2005 |
| CA | 2402101 C | 1/2007 |
| CA | 2549323 C | 7/2009 |
| EP | 541063 A2 | 5/1993 |
| EP | 541063 A3 | 10/1993 |
| EP | 541063 B1 | 9/1998 |
| JP | H02277459 A | 11/1990 |
| JP | 10502549 A | 3/1998 |
| JP | 11512641 A | 11/1999 |
| JP | H11512641 A | 11/1999 |
| JP | 200151335 A | 9/2001 |
| JP | 200250262 A | 1/2002 |
| JP | 200351212 A | 4/2003 |
| JP | 200550820 A | 3/2005 |
| SU | 1468511 A1 | 3/1989 |
| WO | 9310714 A1 | 6/1993 |
| WO | 199301071 A1 | 6/1993 |
| WO | 1996001599 A1 | 1/1996 |
| WO | 9912478 A1 | 3/1999 |
| WO | 199901247 A1 | 3/1999 |
| WO | 0072909 A1 | 12/2000 |
| WO | 200007290 A1 | 12/2000 |
| WO | 2002071977 A2 | 9/2002 |
| WO | 2002071977 A3 | 6/2003 |
| WO | 2005099365 A2 | 10/2005 |

OTHER PUBLICATIONS

"Transcatheter Closure of Atrial Septal Defects" by Larry A. Latson, from pp. 335-348 Transcatheter Therapy in Pediatric Cardiology—1993.

Transcatheter Closure of Heart Defects: Role of Buttoned Devices by P. Syamasundar Rao and E.B. Sideris.

\* cited by examiner

PERCUTANEOUS CATHETER DIRECTED INTRAVASCULAR OCCLUSION DEVICES

CROSS-REFERENCE TO RELATED APPLICATIONS

This application is a continuation of U.S. application Ser. No. 16/179,503, filed Nov. 2, 2018, which is a continuation of U.S. application Ser. No. 14/593,039 (now U.S. Pat. No. 10,149,669), filed Jan. 9, 2015, which is a continuation of U.S. application Ser. No. 13/837,351 (now U.S. Pat. No. 8,961,556), filed Mar. 15, 2013, which is a continuation of U.S. application Ser. No. 13/216,784 (now U.S. Pat. No. 8,454,633), filed Aug. 24, 2011, which is a divisional of U.S. application Ser. No. 11/827,590 (now U.S. Pat. No. 8,034,061), filed Jul. 12, 2007, which are hereby incorporated herein in their entirety by reference.

BACKGROUND OF THE INVENTION

Field of the Invention

The present invention generally relates to intravascular devices for treating certain medical conditions and, more particularly, relates to intravascular occlusion devices for selective occlusion of a vessel anywhere in the body's circulatory system where it is desired to stop the flow of blood. The devices made in accordance with the invention are particularly well suited for delivery through a catheter or the like to a remote location in a patient's vascular system within a patient's body whereby a passageway to be occluded, has an axis and at least one aperture which intersects another vessel wall somewhat perpendicular to the axis.

Description of the Related Art

A wide variety of intravascular devices are used in various medical procedures. Certain intravascular devices, such as catheters and guidewires, are generally used simply to deliver fluids or other medical devices to specific locations within a patient's body, such as a selective site within the vascular system. Other, frequently more complex, devices are used in treating specific conditions, such as devices used in removing vascular occlusions or for treating septal defects and the like.

In certain circumstances, it may be necessary to occlude a patient's vessel, chamber, channel, hole or cavity such as to stop blood flow there through.

Mechanical embolization devices are well known in the art and sold commercially for occlusion of vessels in various locations within the vasculature. U.S. Pat. No. 6,123,715 by Amplatz and U.S. Pat. No. 5,725,552 by Kotula disclose intravascular occlusion devices fabricated from Nitinol braided metal fabric which are heat-set in molds to an expanded shape, but which can be compressed for delivery through a catheter to a treatment site, whereby the device, when urged out of the delivery catheter, self expands within the vasculature to occlude blood flow at the treatment site. The details of the various designs and configurations, as well as methods of fabricating and using the devices, are detailed in the aforementioned patents and incorporated in total herein by reference.

Although the occlusion devices described by Amplatz and Kotula patents are quite effective, there are significant improvements that can be made. In the Amplatz U.S. Pat. No. 5,725,552, there are described, in FIGS. 6A-C, and 11-18, two occlusion devices, each of which incorporates disk elements at one or both ends. The devices further incorporate a cylindrical portion with a diameter smaller than the disk maximum diameter and extending with an axis generally perpendicular to the plane of the disk. An example of this prior art is shown in FIGS. 1A, 1B and 2 hereof. The mentioned prior art devices do not always align themselves as well as possible to the anatomical conditions due to the lack of bending flexibility between the cylindrical portion and the disk portion. This occurs when the vessel wall containing the aperture of the vessel to be occluded is not quite perpendicular to the axis of the vessel to be occluded. In the case of double disked occluders for use, for example, in Ventricular Septal Defects (VSD), Atrial Septal Defects (ASD) and Patent Foraman Ovale (PFO) and the like, it may be that neither wall is perpendicular to the passageway or aperture to be occluded. When this occurs, with the prior art devices, the disk attempts to align, but it's lack of flexibility causes portions of the disk to extend further from the vessel wall than desired which may interfere with blood flow or cause gaps between portions of the disk and the vessel wall.

The prior art devices represented by the Amplatz and Kotula patents, with a single disk, are retained in place, as deployed, by sizing the cylindrical portion diameter larger in its unrestrained self expanding condition larger than the diameter of the vessel to be occluded. This imparts a load from the Nitinol braid's desire to expand larger to be imparted against the body lumen tissue to secure the device in place. Due to lack of precision in estimating the diameter of the vessel to be occluded or the body's ability to yield or dilate in response to pressure changes, and movement of the body, the retention force can occasionally be insufficient to retain the device in place as desired.

Accordingly, it would be advantageous to provide an improved occlusion device which offers increased flexibility between the disk and the cylindrical diameter for better disk alignment to the aperture wall and also to improve the retention of the device, particularly in a single disk occluder device.

SUMMARY

The present invention is well suited for the selective occlusion of a vessel, lumen, channel, or cavity having an axis and at least one aperture which intersects another vessel wall somewhat perpendicular (+ or 45 degrees) to the axis. One example, without limitation, of such a condition is a Patent Ductus Arteriosus (hereinafter PDA). Another example is a vessel, lumen, channel, or hole through which blood flows from one vessel to another vessel such as an Atrial Septal Defect (herein after ASD) or a Ventricular Septal Defect (herein after VSD). Another example could be an arterial venous fistula (AVF) or arterial venous malformation (AVM).

When forming these intravascular devices from a resilient metal fabric, a plurality of resilient strands is provided, with the wires being formed by braiding to create a resilient metallic fabric which can be heat treated to substantially set a desired shape. This braided fabric is then deformed to generally conform to a molding surface of a molding element and the braided fabric is heat treated in contact with the surface of the molding element at an elevated temperature. The time and temperature of the heat treatment is selected to substantially set the braided fabric in its deformed state. After the heat treatment, the fabric is removed from contact with the molding element and will substantially retain its shape in the deformed state. The braided fabric, so treated, defines an expanded state of a medical device which can be deployed through a catheter into a channel in a patient's body.

Embodiments of the present invention provide specific shape improvements over prior art medical devices to address occlusion of vessels having specific anatomical conditions. Such devices of the present invention are formed of a braided metal fabric and have an expanded configuration and a collapsed configuration. In use, a guide catheter can be positioned in a channel in a patient's body and advanced to position the distal end of the catheter adjacent a treatment site for treating a physiological condition. A medical device, formed in a predetermined shape, and made in accordance with the process outlined above, can be collapsed and inserted into the lumen of the catheter. The device is urged through the catheter and out the distal end, whereupon, due to its memory property, it will tend to substantially return to its expanded state adjacent the treatment site. In accordance with a first of these embodiments, a generally elongate medical device has a generally cylindrical middle portion and a pair of expanded diameter disk portions, with one expanded diameter portion positioned at either end of the middle portion. In another embodiment, the medical device is generally bell-shaped, having an elongate cylindrical portion having a tapered first end and a larger diameter second disked end, the second end presenting a fabric disc which will be oriented generally perpendicular to an axis of a vessel, channel, lumen, or cavity when deployed therein.

The inventive device improves the flexibility between the disk portion and the cylindrical middle portion by providing a very small transition diameter between the disk portion and middle portion, the transition diameter being much smaller than the middle portion diameter. This small transition diameter allows the disk to easily flex about this diameter to orient itself to the wall of the vessel containing the aperture to accommodate a wide range of anatomical variations between the axis of the lumen to be occluded and the wall containing the aperture to the lumen.

By recessing the portion having the small transition diameter within an indentation formed in the end of the cylindrical middle portion of the device, exact positioning of the device within a vessel is not overly critical. The recess allows the disk and cylindrical portion to remain in close proximity as they are in free space or will also allow the disk and cylindrical portion to separate a small distance while still maintaining device function.

The improved single disk device also has improved retention when compared to the prior art by the addition of flexible Nitinol shape memory wires sutured or fastened to or a part of the braided structure middle portion. The wires have a resilient hook end, designed to extend outward from the device middle portion surface, upon deployment, to reversibly engage the vessel wall to resist motion of the device toward the disk end. The hook end has no barb and allows the device to be repositioned by device movement opposite in direction (away from disk) to the pointed end of the hook. The device may also be withdrawn back into the delivery catheter after deployment by resiliently un-bending the hook as it is drawn back into the distal end of the catheter. The hook shaped wires add additional device retention to that provided by the sizing of the middle portion diameter larger than the vessel to be occluded.

DETAILED DESCRIPTION

Figure 1A:
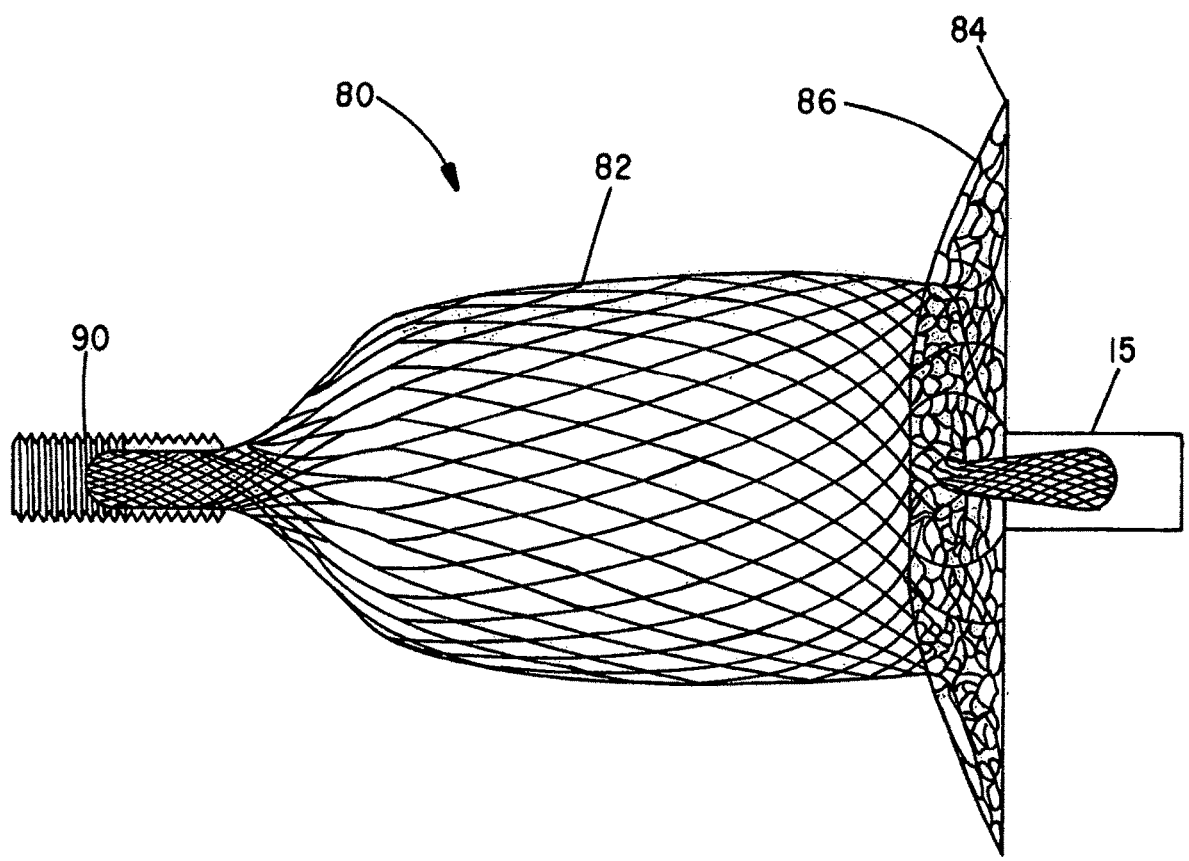
FIGS. 1A and 1B depict the prior art single disk occluder device.

The present invention provides an improved percutaneous catheter directed intravascular occlusion device for use in the vasculature in patients' bodies, such as blood vessels, channels, lumens, a hole through tissue, cavities and the like. In forming a medical device of the invention, a metal fabric is formed of a plurality of wire strands having a predetermined relative orientation between the strands.

The metal strands define two sets of essentially parallel generally helical strands, with the strands of one set having a "hand", i.e. a direction of rotation, opposite that of the other set. This defines a generally tubular fabric, known in the fabric industry as a tubular braid. The Amplatz and Kotula patents previously discussed describe medical devices and the methods of fabrication of such devices in great detail and detailed further discussion is not needed.

The pitch of the wire strands (i.e. the angle defined between the turns of the wire and the axis of the braid) and the pick of the fabric (i.e. the number of wire crossovers per unit length) may be adjusted as desired for a particular application. The wire strands of the metal fabric used in the present method should be formed of a material which is both resilient and which can be heat treated to substantially set a desired shape. Materials which are suitable for this purpose include a cobalt-based low thermal expansion alloy referred to in the field as Elgeloy, nickel-based high temperature high-strength "superalloys" commercially available from Haynes International under the trade name Hastelloy, nickel-based heat treatable alloys sold under the name Incoloy by International Nickel, and a number of different grades of stainless steel. The important factor in choosing a suitable material for the wires is that the wires retain a suitable amount of the deformation induced by the molding surface (as described below) when subjected to a predetermined heat treatment.

One class of materials which meet these qualifications is so-called shape memory alloys. One particularly preferred shape memory alloy for use in the present method is Nitinol. NiTi alloys are also very elastic—they are said to be "superelastic" or "pseudoelastic". This elasticity will help a device of the invention return to a present expanded configuration for deployment following passage in a distorted form through a delivery catheter.

In forming a medical device in keeping with the invention, an appropriately sized piece of the metal fabric is cut from the larger piece of fabric which is formed, for example, by braiding wire strands to form a long tubular braid. When cutting the fabric to the desired dimensions, care should be taken to ensure that the fabric will not unravel.

One can solder, braze, weld or otherwise affix the ends of the desired length together (e.g. with a biocompatible cementitious organic material) before cutting the braid.

Once an appropriately sized piece of the metal fabric is obtained, the fabric is deformed to generally conform to a surface of a molding element. Deforming the fabric will reorient the relative positions of the strands of the metal fabric from their initial order to a second, reoriented configuration. The shape of the molding element should be selected to deform the fabric into substantially the shape of the desired medical device when unconstrained.

Once the molding element is assembled with the metal fabric generally conforming to a molding surface of that element, the fabric can be subjected to a heat treatment while it remains in contact with that molding surface. Suitable heat treatments of Nitinol wire to set a desired shape are well known in the art. It has been found that holding a Nitinol fabric at about 500° C. to about 550° C. for a period of about 1 to about 30 minutes, depending on the softness or harness of the device to be made, will tend to set the fabric in its deformed state, i.e. wherein it conforms to the molding surface of the molding element. At lower temperatures the heat treatment time will tend to be greater (e.g. about one hour at about 350° C.) and at higher temperatures the time will tend to be shorter (e.g. about 30 seconds at about 900° C.).

After the heat treatment, the fabric is removed from contact with the molding element and will substantially retain its shape in a deformed state.

Figure 5A:
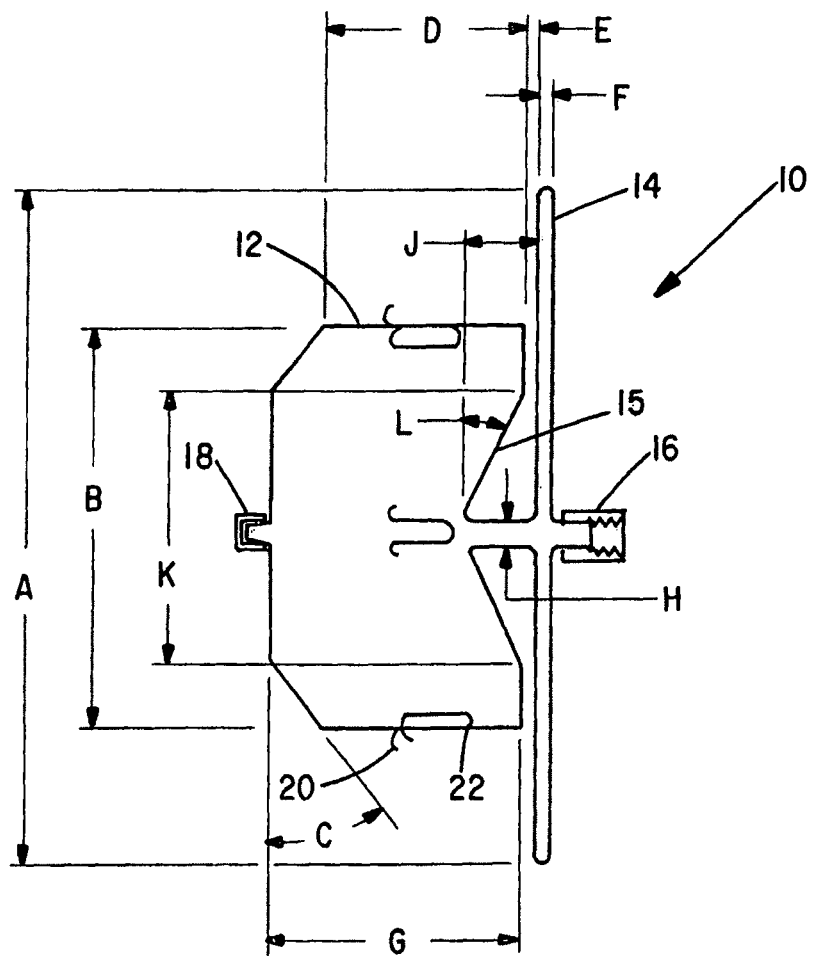
FIG. 5A is a cross-sectional view of a single disk device in accordance with the present invention.
Figure 5B:
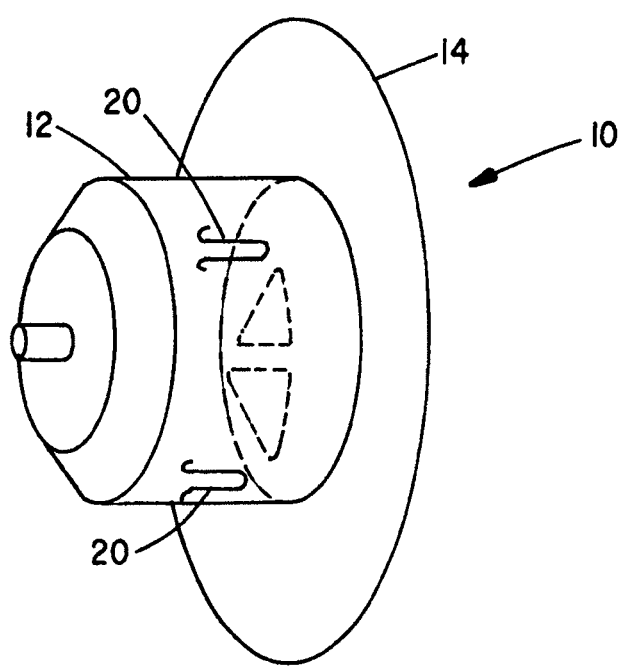
FIG. 5B is a perspective view of the inventive device of FIG. 5A.

FIGS. 5A and 5B illustrate an embodiment of a medical device 10 in accordance with the present invention. This device 10 has a generally cylindrical body portion 12 and an outwardly extending forward disk end 14. The cylindrical body portion 12 is sized to be somewhat larger (about 10-30%), than the vessel to be occluded. This sizing is intended to provide one element of anchoring the device to prevent dislodgement. The disk portion of the device 14 is intended to abut the adjacent wall surrounding, the aperture, to prevent device movement toward the cylindrical portion direction and to assist in sealing the aperture.

The improvement over the prior art incorporates a transition diameter H, between the cylindrical portion 12, and the disk portion 14 that is small in relationship to the cylindrical diameter B, and the disk diameter A. This small transition diameter allows the disk portion to easily orient itself to the vessel wall containing the aperture where the wall is not truly perpendicular (perpendicular + or −45 degrees). Additionally, the recessed transition diameter H within an indentation 15 in the end of the cylindrical body will allow the device to conform to the anatomy in which the device is being positioned by acting like a spring member for maintaining tension between the disk and the cylindrical body. Separation between the disk and the cylindrical body will not impact device performance.

One application, for which this device is particularly well suited, is occluding vessels, channels, lumens or cavities that are connected by aperture to another vessel having a wall surrounding the aperture. One such condition known in the art is a patent ductus arteriosus (PDA) which is essentially a condition wherein two blood vessels, most commonly the aorta and pulmonary artery adjacent the heart, have a blood flow shunt between their lumens. Blood can flow directly between these two blood vessels through the passageway, compromising the normal flow of blood through the patient's vessels. Other physiologic conditions in the body occur where it is also desirous to occlude a vessel to prevent blood flow through the vessel. This device embodiment may be used anywhere in the vasculature where the anatomical conditions are appropriate for the design.

As explained more fully below in connection with FIGS. 5A and 5B, the cylindrical shaped body 12 is adapted to be deployed within the vessel to be occluded, while the disk 14 is adapted to be positioned adjacent the wall surrounding the aperture associated with the vessel to be occluded. The braided metal fabric extends from the proximal disk end clamp 16, radially outward to the disk maximum diameter A and back radially inward against itself to the transitional diameter H. The transitional diameter extends distally a distance J whereby the fabric forms a reverse cone toward the disk with a diameter K where the fabric turns to follow parallel to the disk but spaced from the disk a distance E, radially outward to a diameter B. The fabric continues to maintain cylindrical diameter B distally a distance D, then forming a taper surface of angle C to a total cylindrical portion length G. The distal end clamp 18 and the proximal end clamp 16 hold the braided wire ends from unraveling. The proximal end clamp 16 also contains a threaded portion that reversibly connects to a delivery system (not shown) such as a cable or shaft with mating threads at its end.

Figure 1B:
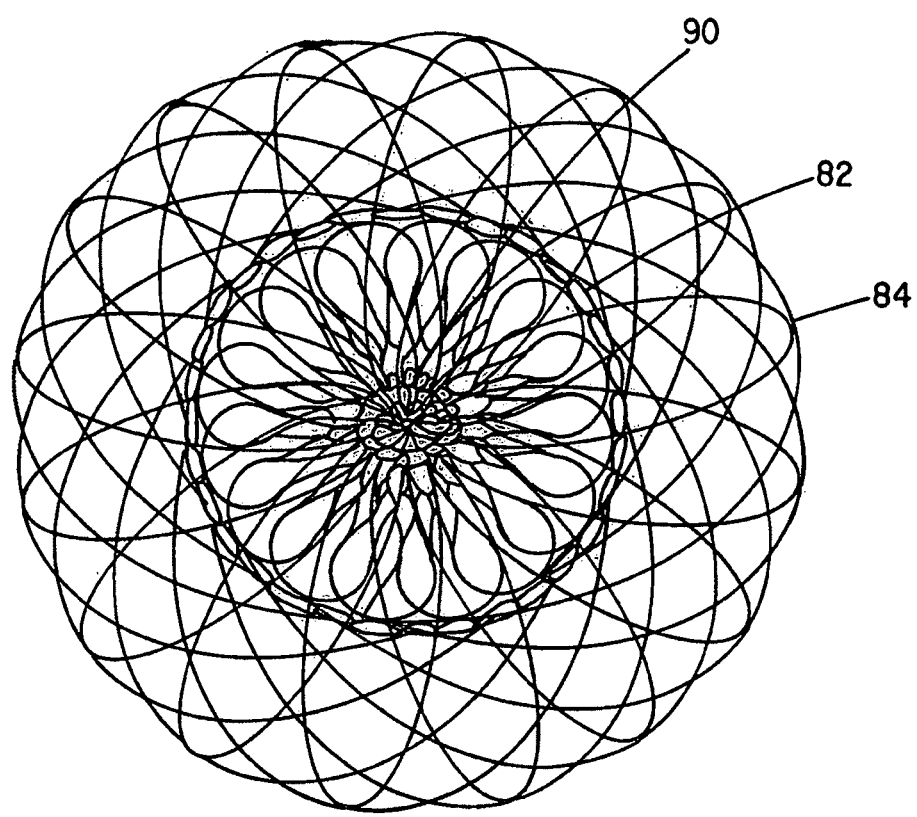

The improvement in disk flexibility and conformance to a vessel wall which are not perpendicular to the axis of the vessel to be occluded comes from the disk maximum diameter A in relation to the small diameter H, or the ratio of A/H. In the prior art device of FIGS. 1A and 1B this ratio is about 1.9, but in the improved design of FIGS. 5A and 5B the ratio is in the range of 3 to 30, preferably about 10 to 20-25. In the prior art design, the ratio for the cylindrical body 12 diameter B to the disk transition diameter H is 1.0 since there is no reduced transition diameter. In the improved design, the ratio B/H is in the range of 2-25 and preferably 10-20. This improved ratio reduces the bending force necessary to cause disk alignment to the vessel wall or alternatively, alignment of the cylindrical portion to the vessel to be occluded. The transition diameter H has a length J which is about 2-5 times the diameter H. This length J is necessary to allow a small dimension E between the disk inner surface and the cylindrical portion proximal end wall as shown in FIG. 5A. This improves the device fit and improves the sealing of the device. To accommodate the length J of transition diameter H the fabric is shaped to form a conical surface at an angle L to the proximal end wall of the cylindrical portion. This conical surface accommodates user displacement of the cylindrical portion from adjacent the disk by cone flattening and thereby provides increased radial expansive force for device retention on the proximal cylindrical outer diameter. Additionally, the conical surface acts as a spring to provide axial tension between the disk and cylindrical portion when they are displaced apart to keep the hooks 20 engaged in the wall of the vessel being occluded, thus improving device retention.

may vary from 30 to 100 and preferably from 50 to 80 and for a PDA device is preferably 70.

The sizes of the body 12 and the disk 14 and device length can be varied as desired for differently sized vessels, channels, lumens or cavities. A table of dimensional ranges and for select devices is provided below in mm.

TABLE 1

|  | A | B | C | D | E | F | G | H | J | K | L |
|---|---|---|---|---|---|---|---|---|---|---|---|
| Range | 6 to 35 | 2 to 28 | 20 to 70 | 2 to 20 | 0 to 6 | 1 to 3 | 3 to 25 | 1 to 8 | 0 to 10 | 3 to 20 | 20 to 70 |
| PDA | 8 | 4 | 45 | 4 | 1 | 1 | 6 | 1 | 2 | 3 | 20 |
| Another | 23 | 18 | 45 | 10 | 0 | 2 | 14 | 2 | 4 | 8 | 30 |

As shown in FIGS. 5A and 5B, retention hooks 20 are preferably fabricated from Nitinol wire heat set into a hook shape at each end and a bend of about 180 degrees in the mid length segment of the wire to create 2 interconnected hooks. Alternatively, the hooks could be a part of the device—i.e. individual wires within the braided structure that are isolated and formed into hooks. The ends of the hooks are oriented toward the disk and sutured 22 or fastened by any known means to the braided fabric on the cylindrical portion 12 of the device. The hook wires 20 are preferably about 0.007 inches in diameter and 3 mm in length and flexible enough to be back loaded into the delivery catheter or forward loaded, if introduced in a straightened out configuration. The device may have any number of these hooks, but preferably has three pairs of hooks. The number of hooks would preferably range from 6 to 12. The hooks assist in the retention of the device by resisting motion of the device in the vessel in a direction that would cause the hooks to engage the tissue. The hooks 20 do not have barbs so that the engagement is reversible by movement of the device opposite to the open end of the hook. The art pertaining to vascular grafts has many examples of alternative hooks that may be incorporated into vascular implantable devices.

Figure 6:
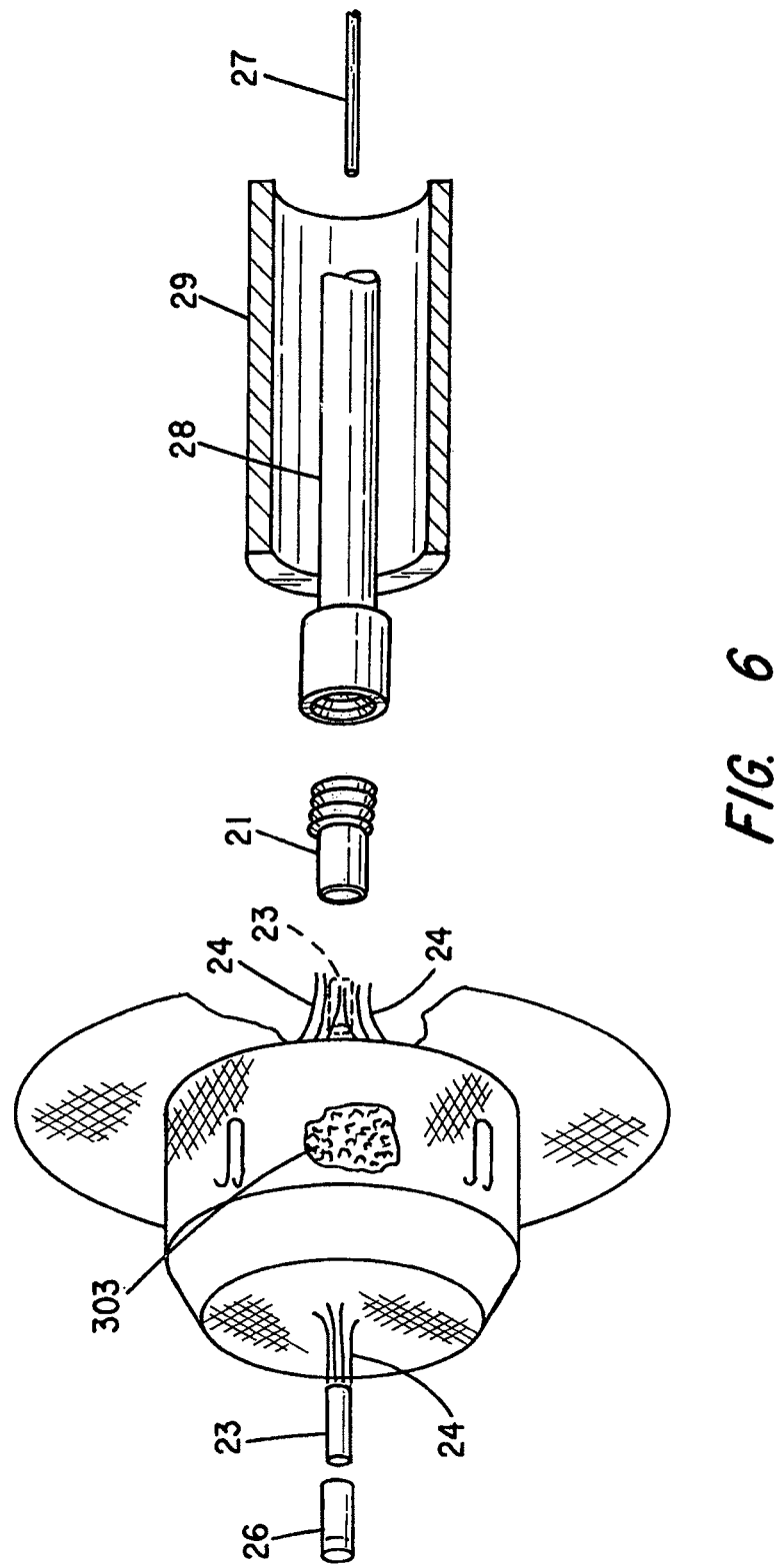
FIG. 6 is a partially exploded assembly view of an alternative single disk device and delivery apparatus.

Those skilled in the art will appreciate that, in order to speed up the occlusion of the vessel device, the device may be coated with a suitable thrombogenic agent, filled with a polyester fiber or braided with an increased number of wire strands. The prior art devices have preferably used a polyester fiber (303 as shown in FIG. 6) within the braided device. This fiber easily collapses with the device for delivery through a catheter. The interwoven fiber by attachment to clot retains the clot firmly within the device as it forms the occlusion.

The delivery device 28 shown in FIG. 6 can be used to urge the PDA occlusion device 10 through the lumen of a catheter or long introducer sheath for deployment in a channel of the patient's body. When the device is deployed out the distal end of the catheter, the device will still be retained by the delivery device. Once the proper position of the device 10 in the vessel is confirmed, the shaft of the delivery device 28 can be rotated about its axis to unscrew the clamp 16 from the threaded end of delivery means. Of course the threaded connection could be at either end of the device depending on the anatomical situation and the desired or available means of access to the treatment site.

The tubular braid used to fabricate occlusion devices of this invention may range from wire having a diameter of 0.002 to 0.005 in., preferably in the range of 0.003 to 0.0035 in., and for a PDA device, preferably 0.003 in. diameter. The number of wires in the tubular braid may vary from 36 to 144 but preferably is in the range of 72 to 144 and for a PDA device is preferably 144 wires. The pick count of the braid By keeping the PDA device 10 attached to the delivery means, the operator may still retract the device back into a delivery sheath for repositioning if it is determined that the device is not properly positioned in the first attempt. This threaded attachment will also allow the operator to control the manner in which the device 10 is deployed out of the distal end of the delivery catheter. As explained below, when the device exits the delivery catheter it will tend to resiliently return to a preferred expanded shape which was set when the fabric was heat treated. When the device springs back into this shape, it may tend to act against the distal end of the catheter, effectively urging itself forward beyond the end of the catheter. This spring action could conceivably result in improper positioning of the device. Since the threaded clamp 16 can enable the operator to maintain a hold on the device during deployment, the spring action of the device can be controlled and the operator can control the deployment to ensure proper positioning.

Optionally, but not considered a requirement, the device as shown in FIG. 6, could be configured with a hollow inner clamp member 23 at both wire ends and a outer clamp proximal member 21 and a distal outer clamp member 26. The wire ends 24 are crimped between the inner and outer clamp members 21, 26 by swaging or alternatively may be bonded or welded between the clamp members. The inner clamp member is tubular and is sized with an inside diameter to freely pass a push wire 27. The distal outer clamp member 26 is sized with an inside diameter sufficient to accommodate the braid wire ends 24 surrounding the inner clamp member prior to swaging. The distal end on the distal outer clamp member 26 is solid (closed end) to accept the push force from the push wire 27 placed through both inner clamp members against this solid end. The proximal outer clamp member 21 is shown with external threads to reversibly connect to the delivery system 28, which is preferably a nylon block co-polymer such as Pebax with a 0.001 in. braided wire over the Pebax inner tube extrusion, followed by another outer layer of Pebax to cover the braid. The delivery catheter/sheath 29 may be similarly constructed except larger in diameter to accommodate the passage of the device 10 and delivery system 28. Such construction is typical in intravascular catheters where a flexibility and torque transmission are needed.

Optionally, the delivery catheter sheath 29 may have a 0.001 in. thick layer of PTFE to lower friction for ease of device passage therethrough. The hollow delivery system sized to allow a push wire 27, made of stainless steel 0.008-0.014 in. to pass through the delivery system and the proximal clamp and to engage the distal clamp to push the distal clamp away from the proximal clamp to elongate the device, facilitate release of the hooks and facilitate recapture of the device into the delivery sheath 29. The distal end of the push wire 27 and the distal inner clamp 23 may be designed to attach by a threaded connection or other reversible means to ensure the wire does not inadvertently get positioned proximal to the distal inner clamp 23. It is also anticipated that a spring positioned between the delivery system 28 and the push wire 27 could maintain the push wire against the distal outer clamp 26. By means of the delivery system 28 maintaining control of the proximal end of the device 10 and the push wire 27 being able to exert a push force on the distal end of the device, the device may be elongated or allowed to self expand and contract in length as desired. This aids in repositioning with the hooks being easily released by pushing on the push wire to force the device in the distal direction. This also aids in withdrawing the device back into the sheath 29 should the need occur, such as in incorrect device sizing to the anatomy.

Figure 7A:
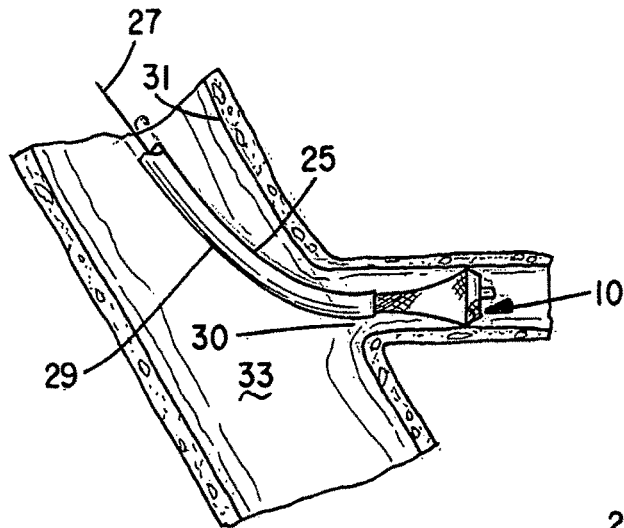
FIGS. 7A through 7C depict progressive stages of deployment of the single disk occluder of FIGS. 5A and 5B.
Figure 7B:
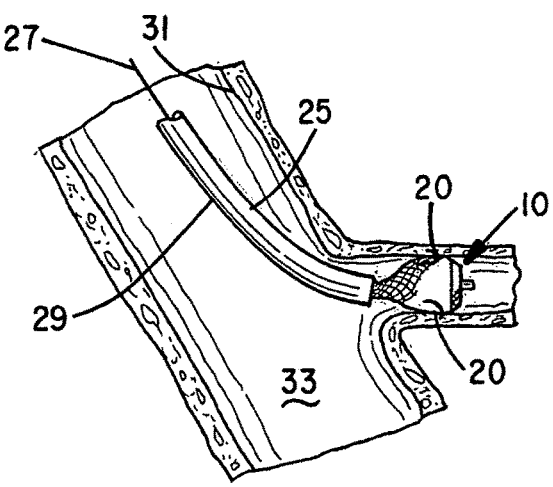
Figure 7C:
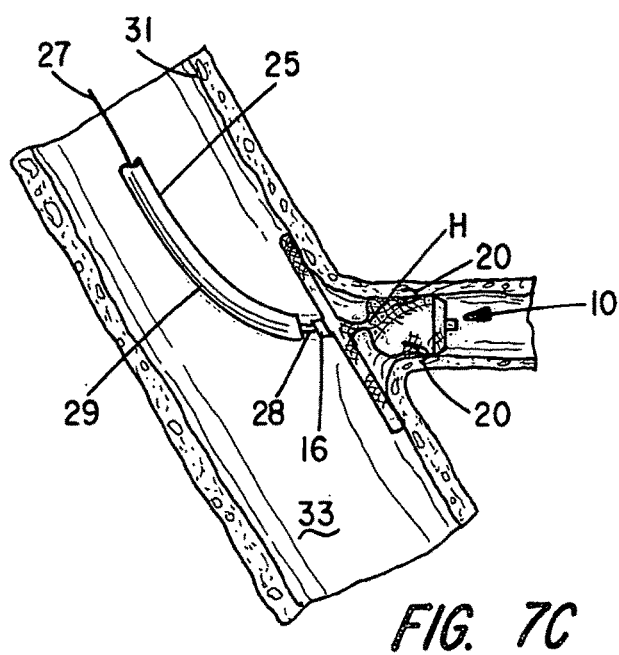

FIGS. 7A-C schematically illustrates how a medical device 10, generally as outlined above, can be used to occlude a vessel having a wall surrounding an aperture to a vessel, channel, lumen, or cavity which is to be occluded. The device 10, in its collapsed for delivery configuration and attached to the delivery system 28, can be passed through a delivery catheter 29 such that the distal end of the delivery catheter is adjacent the aperture 30 in the vessel wall 31 as shown in FIG. 7A. The delivery system 28 is advanced distally while holding back the delivery catheter 29 to urge the distal end of the device 10 out from the catheter 29 to elastically self expand substantially to its predetermined heat set molded state, where by it contacts the vessel wall. At this point the distal end of catheter 29 may react to the expansion force and move proximally a small amount as shown in FIG. 7B. The hooks 20 begin to make contact with the vessel wall to hold the device in place. If needed to be positioned distally this can be done because the hooks will release in that direction. In FIG. 7C the device is full exited from the catheter 29 but still attached to the delivery system 28. As shown in this figure the disk 14 self aligns with the wall 31 by pivoting about the small diameter H. After the device is positioned as desired, the delivery system is disconnected by turning the delivery system 28 in a direction to release the threaded connection at the proximal end clamp 16.

The body portion 12 should be sized so that it will frictionally engage the lumen of the vessel to be occluded. The device 10 will then be held in place by the combination of the friction between the body portion and the lumen of the vessel and the hooks 20 which engage the wall. Over a relatively short period of time, thrombi will form in and on the device 10 and the thrombi will occlude the vessel. Those skilled in the art will appreciate that in order to speed up the occlusion of the vessel device, the device may be coated with a suitable thrombogenic agent, filled with a polyester fiber or braided with an increased number of wire strands.

Pulmonary vascular occlusive disease and pulmonary atrial hypertension develops in adulthood. Patients with secundum atrial septal defect (ASD) with a significant shunt are operated upon ideally at five years of age or whenever a diagnosis is made in later years. With the advent of two dimensional echocardiography and Doppler color flow mapping, the exact anatomy of the defect can be visualized. The size of the defect will correspond to the selected size of the ASD occlusive device to be used.

Figure 2:
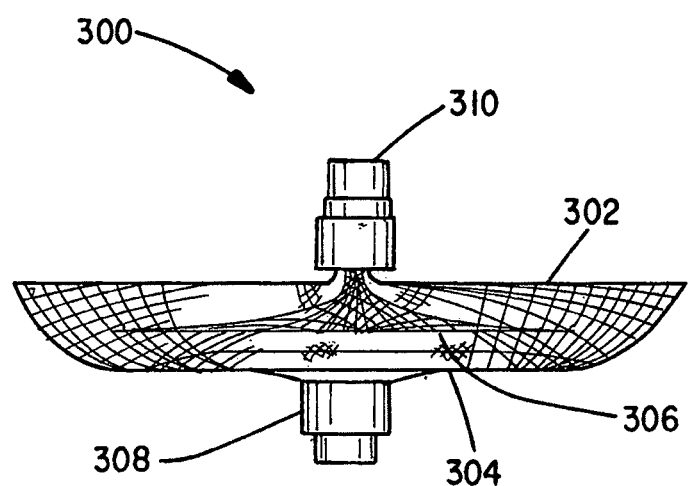
FIG. 2 is an enlarged side elevation view of another prior art device.
Figure 3:
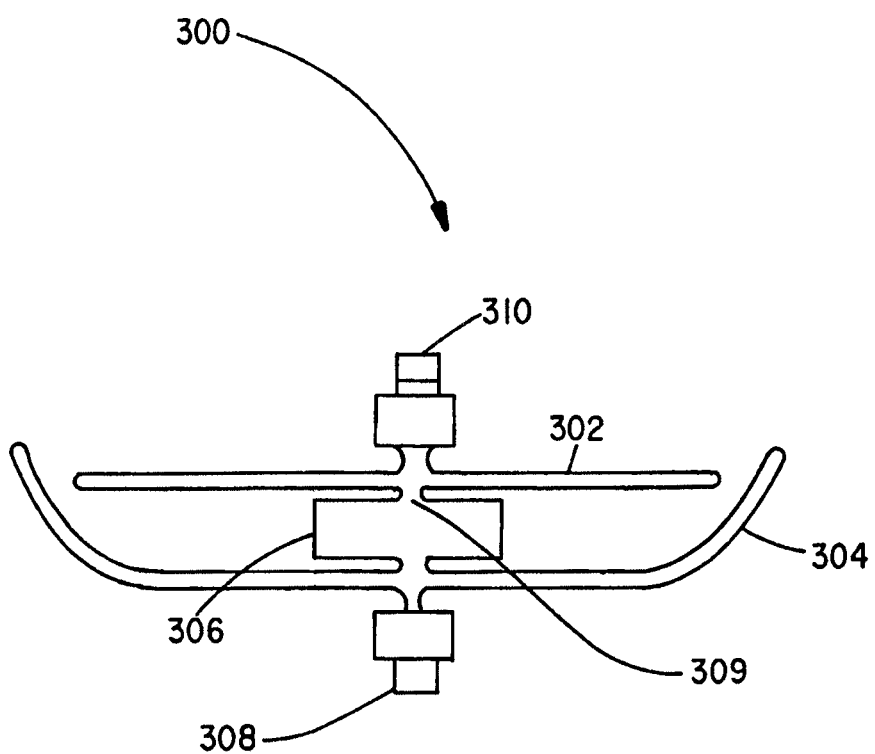
FIG. 3 is a cross-sectional view of the device like that of FIG. 2 but showing the inventive modification for improved disk flexibility for alignment to anatomy variations.
Figure 4:
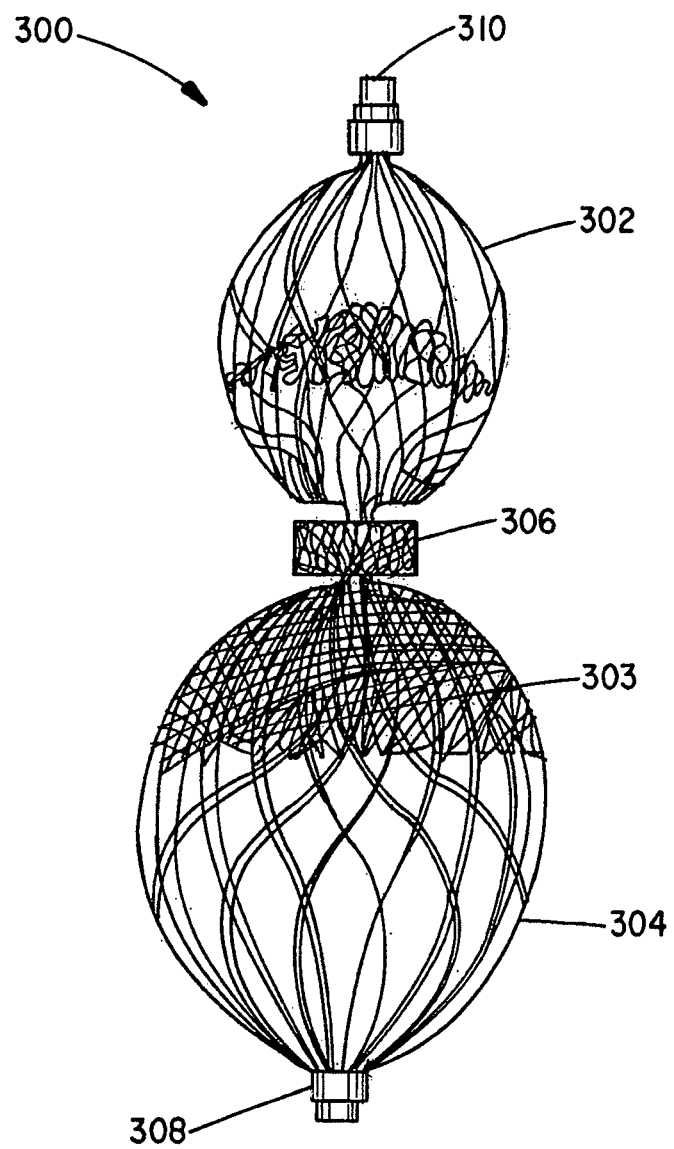
FIG. 4 is a side elevational view of the prior art ASD device, shown stretched and filled with polyester fibers.

FIGS. 2 through 4 illustrate an alternate preferred embodiment of a medical occlusive device in accordance with the present invention for correcting an ASD. It is proposed that this device 300 may also be well suited in occluding defects known in the art as patent foraman ovale (hereinafter PFO) or for ventricular septal defects (VSD).

With reference to FIGS. 2-4, the device 300 in its relaxed, unstretched state has two disks 302 and 304 aligned in spaced relation, linked together by a short cylinder 306. The length of the cylindrical segment 306 preferably approximates the thickness of the atrial septum, and ranges between 2 to 20 mm. The proximal 302 and distal 304 disks preferably have an outer diameter sufficiently larger than the shunt to prevent dislodging of the device. The proximal disk 302 has a relatively flat configuration, whereas the distal disk 304 is cupped towards the proximal end slightly overlapping the proximal disk 302. The improvement in the device design over the prior art is shown in FIG. 3 which is a cross-sectional view of the device of FIG. 2. In the prior art design, the fabric of the short cylinder 306 connected with the inside wall fabric of each disk at the diameter of the short cylinder. In the improved device design of the present invention, the short cylinder connects with the disk walls at a small diameter 309 which is much smaller than the diameter of the short cylinder which is much smaller than the diameter of the disk. This allows the disk to easily pivot about diameter 309 to allow the disks to align themselves with anatomical vessel walls that are not perpendicular (at an angle) to the aperture there between.

The ends of this braided metal fabric device 300 are welded or clamped together with clamps 308 and 310, as described above, to avoid fraying. Of course the ends may alternately be held together by other means readily known to those skilled in the art. The clamp 310 tying together the wire strands at the proximal end also serves to connect the device to a delivery system. In the embodiment shown, the clamp 310 is generally cylindrical in shape and has a recess for receiving the ends of the metal fabric to substantially prevent the wires comprising the woven fabric from moving relative to one another. The clamp 310 also has a threaded surface within the recess. The threaded recess is adapted to receive and engage the threaded distal end of a delivery device 28 (FIG. 6).

The ASD occlusion device 300 of this embodiment of the invention can advantageously be made in accordance with the method outlined above. The device 300 is preferably made from a 0.005 inch Nitinol wire mesh. The braiding of the wire mesh may be carried out with 28 picks per inch at a shield angle of about 64 degrees using a Maypole braider with 72 wire carriers. The stiffness of the ASD device 300 may be increased or decreased by altering the wire size, the shield angle, the pick size, the number of wire carriers or the heat treatment process.

Those skilled in the art will recognize from the preceding discussion that the cavities of the mold must be shaped consistent with the desired shape of the ASD device. In the case of the improvement the mold must be shaped to provide for forming the small pivot diameter 309.

Figure 8A:
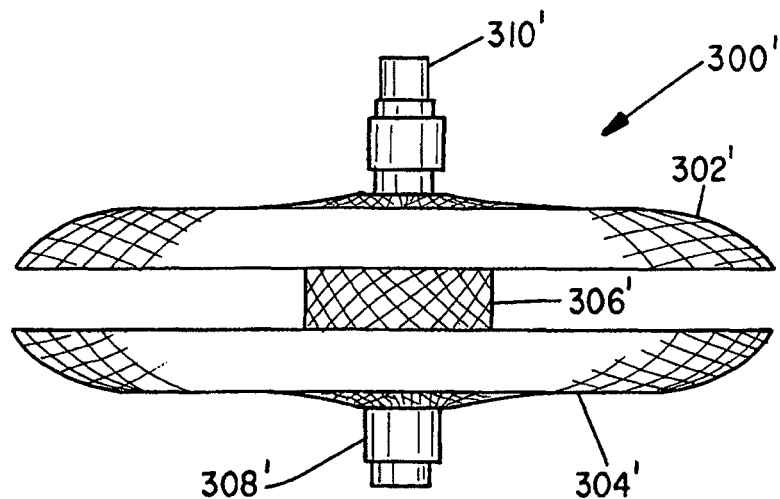
FIG. 8A depicts an ASD or VSD occluder made in accordance with the present invention shown in its pre-shaped configuration having double disks of the same diameter, each disk dished inward with a gap between the disks.
Figure 8B:
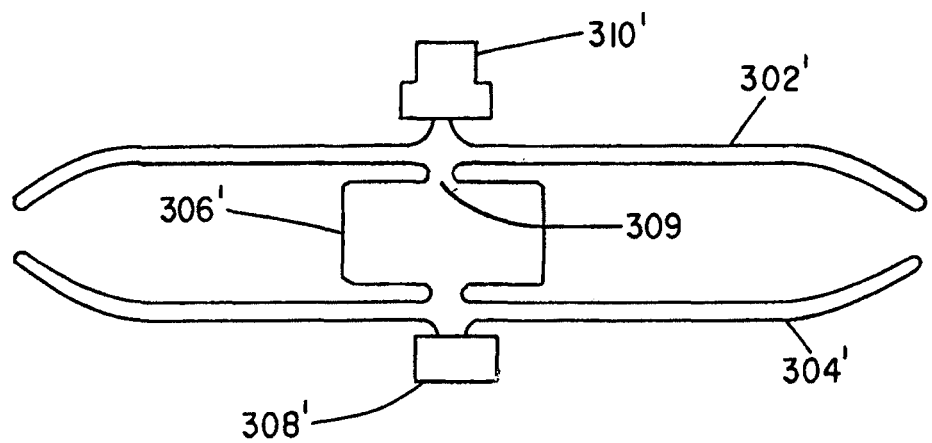
FIG. 8B is a cross-sectional view of the device of FIG. 8A showing the inventive modification for improved disk flexibility and alignment to anatomy.
Figure 8C:
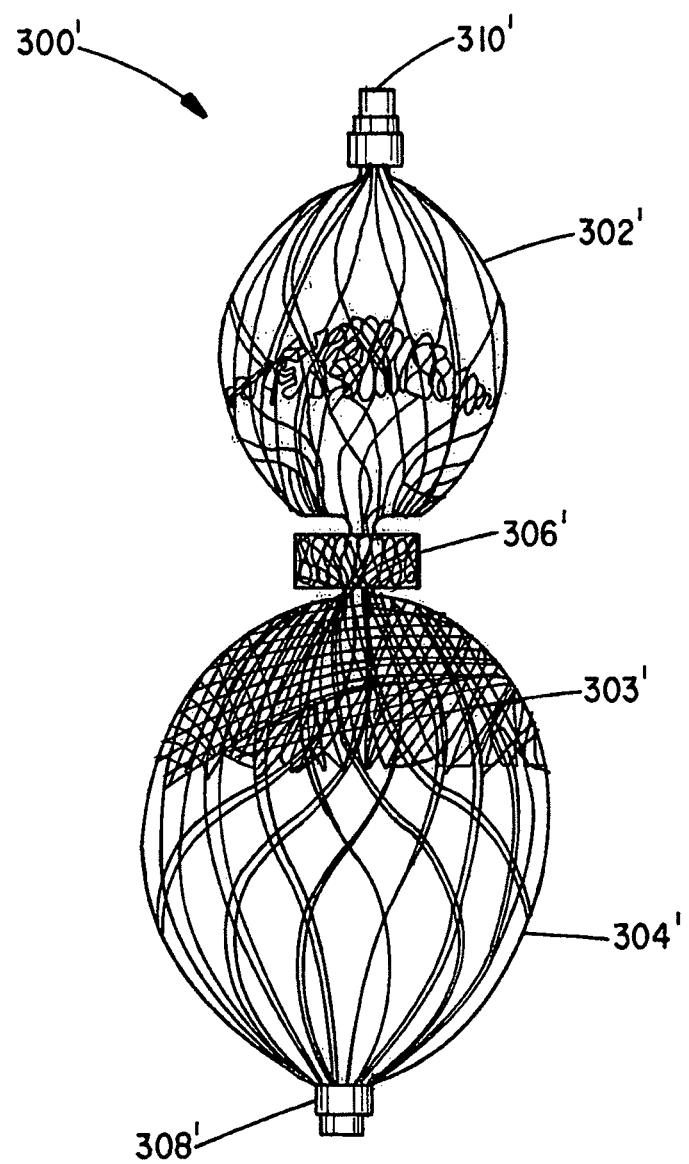
FIG. 8C is a cross-sectional view of the device of FIG. 3 showing the inventive modification to improve disk flexibility and alignment to anatomy variations.

FIGS. 8A through 8C illustrate an ASD device having a modified configuration. The proximal disk 302 is a mirror image of distal disk 304'. The distance separating the proximal and distal disks 302' and 304' is less than the length of the cylindrical segment 306. The cup shape of the disk, as illustrated in FIG. 8B, ensures complete contact between the occlusion device 300' and the atrial septum. As such, a neo endocardium layer of endothelial tissue forms over the occlusion device 300, thereby reducing the chance of bacterial endocarditis.

In order to speed up the occlusion of the vessel device, the device may be coated with a suitable thrombogenic agent, filled with a polyester fiber or braided with an increased number of wire strands. A polyester fiber 303 (as shown in FIGS. 4 and 8*c*) is optionally placed within the braided device to speed the clotting process. This fiber easily collapses with the device for delivery through a catheter and can be placed in the disks, or middle portions or a combination of portions. The interwoven fiber by attachment to clot retains the clot firmly within the device as it forms the occlusion.

Figure 9:
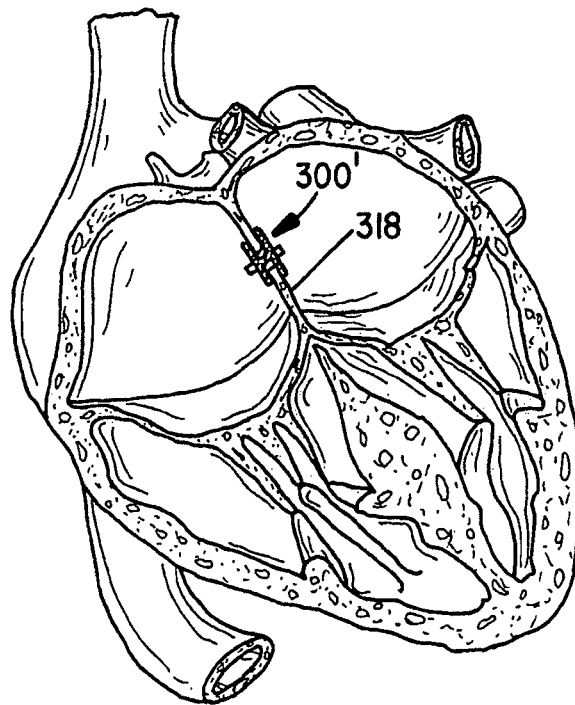
FIG. 9 is a partial sectional side elevational view of the ASD device of FIG. 2-4 shown positioned within an ASD of a patient's heart.

The use of the device will now be discussed in greater detail with reference to FIGS. 9, 10 and the delivery device of FIG. 7C. The device may be delivered and properly placed using two dimensional echocardiography and Doppler color flow mapping. The delivery device 28 of FIG. 7C can take any suitable shape, preferably comprising an elongated flexible metal shaft similar to a conventional guidewire or may be a hollow shaft similar 27 as described for FIG. 6 above. The delivery device 28 is used to advance the ASD occlusion device 300 through the lumen 25 of a small diameter cylindrical tube, such as a delivery catheter 29 for deployment. The ASD device 300' is loaded into the lumen 25 by stretching the same to put it in an elongated condition. The device may be inserted into the lumen 25 during the procedure or preassembled at a manufacturing facility, in that the devices of the present invention do not take on a permanent set when maintained in a compressed state.

Figure 10:
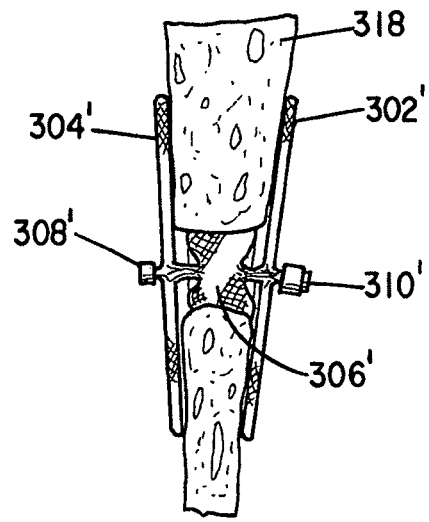
FIG. 10 is a cross-sectional view of an occlusion device of the invention showing the disks conforming to the walls in the occlusion of a VSD.

FIG. 10 illustrates how the disks 302' and 304' can assume a non-parallel relationship to intimately engage opposed walls of a septum 318 of non-uniform thickness and with the central cylindrical portion 306' expanded against the walls defining the ASD. FIG. 10 depicts the inventive device 300' occluding an ASK in the heart.

From a femoral vein approach, the delivery catheter 29 is passed across the ASD. The device 300' is advanced through the delivery catheter until the distal end 304' becomes unconstrained on exiting the end of the catheter, whereupon it assumes its disk-like shape in the left atrium. The delivery catheter 29 is then pulled back in the proximal direction across the ASD and the delivery device 28 is held stationary, urging the distal disk 304' against the septum 318.

The delivery catheter 29 is then further pulled away from the septum 318, allowing the proximal disk 302' to extend out of the delivery catheter 29, where it resiliently returns to its predefined expanded disk-like shape. In this manner, the ASD device 300' is positioned such that the distal disk 304' presses against one side of the septum 318 while the proximal disk 302' presses against the other side of the septum 318.

In order to increase its occluding ability, the device can contain polyester fibers 303'. (See FIG. 8C). In instances where the device is improperly deployed on a first try, the device 300' may be recovered by pulling the delivery device 28 proximally, thereby retracting the device 300' back into the delivery catheter 29 prior to a second attempt at positioning the device 300' relative to the defect.

When the ASD occluding device 300' is properly placed, the physician rotates the delivery device 28, unscrewing the delivery device 28 from the clamp 310' of the occluding device 300'. The threads on the clamp 310' are such that the rotation of the delivery device 28 unscrews the delivery device from the clamp 310' of the occluding device 300', rather than merely rotating the occluding device 300'. As noted above, in alternate embodiments, the threaded clamp can enable the operator to maintain a hold on the device during deployment, or enables the operator to control the spring action during deployment of the device to ensure proper positioning.

Generally, the method in accordance with the present invention further includes a method of treating a physiological condition of a patient. In accordance with this method, a medical device suitable for treating the condition, which may be substantially in accordance with one of the embodiments described in detail above, is selected. For example, if a patent ductus arteriosus is to be treated, the PDA occlusion device 10 of FIGS. 5A, 5B and 6 can be selected. Once the appropriate medical device is selected, a catheter may be positioned within a channel in patient's body to place the distal end of the catheter adjacent the desired treatment site, such as immediately adjacent (or even within) the passageway or channel of the PDA.

The medical device can be collapsed into its collapsed configuration and inserted into the lumen of the catheter. The collapsed configuration of the device may be of any shape suitable for easy passage through the lumen of a catheter and proper deployment out the distal end of the catheter. For example, the devices shown in FIGS. 2, 3, 4, 5A, 5B, 6 and 8A-8C have a relatively elongated collapsed configuration wherein the devices are stretched along their axes as shown in FIGS. 4 and 8C. This collapsed configuration can be achieved simply by stretching the device generally along its axis, e.g. by manually grasping the clamps 308 and 310 and pulling them apart, which will tend to collapse the expanded diameter portions 302 and 304 of the device inwardly toward the device's axis. The PDA occlusion device 10 of FIGS. 2 and 3 also operates in much the same fashion and can be collapsed into its collapsed configuration for insertion into the catheter by applying tension generally along the axis of the device. In this regard, these devices 10 and 300 are not unlike "Chinese handcuffs", which tend to constrict in diameter under axial tension.

Once the medical device is collapsed and inserted into the catheter, it may be urged along the lumen of the catheter toward the distal end of the catheter. This may be accomplished by using a delivery system or the like removably connected to the device to urge it along the catheter. When the device begins to exit the distal end of the catheter, which is positioned adjacent the desired treatment site, it will tend to resiliently return substantially entirely to its preset expanded configuration. Superelastic alloys, such as Nitinol, are particularly useful in this application because of their ability to readily return to a particular configuration after being elastically deformed to a great extent. Hence, simply urging the medical device out of the distal end of the catheter tends to properly deploy the device at the treatment site.

Although the device will tend to resiliently return to its initial expanded configuration (i.e. its shape prior to being collapsed for passage through the catheter), it should be understood that it may not always return entirely to that shape. For example, the member 12 of FIG. 5A is intended to have a maximum outer diameter in its expanded configuration at least as large as and preferably larger than, the inner diameter of the lumen in which it is to be deployed. If such a device is deployed in a vessel having a small lumen, the lumen will prevent the device from completely returning to its expanded configuration. Nonetheless, the device would be properly deployed because it would engage the inner wall of the lumen to seat the device therein, as detailed above.

If the device is to be used to permanently occlude a channel in the patient's body, such as the devices 10 and 300 described above may be, one can simply disconnect the delivery system (example shown FIG. 6) by reversing the reversible connection to the device and retract the catheter and delivery system from the patient's body. This will leave the medical device deployed in the patient's vascular system so that it may occlude the blood vessel or other channel in the patient's body.

While a preferred embodiment of the present invention has been described, it should be understood that various changes, adaptations and modifications may be made therein without departing from the spirit of the invention and the scope of the appended claims.

For example, it is anticipated that in a double disk design that it may be desirable that only one end of the device have a small transition diameter between the disk and the adjacent middle cylindrical portion. It is also anticipated that the cylindrical middle or body portion may be non-concentric to one or both disks. It is further anticipated that the cylindrical portion could be barrel shaped, concave, convex, tapered or a combination of shapes without departing from the invention herein. Likewise the cylindrical portion distal and proximal ends could have differing shapes than the recessed conical shape described while still retaining the benefits described.

The invention claimed is:

1. A collapsible medical device comprising a tubular metal fabric, the tubular metal fabric comprising:
a plurality of braided metal strands and a proximal end and a distal end, the tubular metal fabric having a collapsed configuration for delivery through a channel in a patient's body and an expanded preset configuration for substantially creating an occlusion of an opening in the patient's body, the tubular metal fabric in the expanded preset configuration having two expanded disk portions and a central portion disposed between the two expanded disk portions, a first expanded disk portion of the two expanded disk portions and the central portion connected by a first reduced diameter portion, and a second expanded disk portion of the two expanded disk portions and the central portion connected by a second reduced diameter portion,
wherein each of the first and second reduced diameter portions is smaller in diameter than both the two expanded disk portions and the central portion, and
wherein the central portion includes two concave conical portions, each concave conical portion facing an inner face of a respective one of the expanded disk portions, and wherein each of the first and second reduced diameter portions is at least partially recessed into the central portion within a respective one of the concave conical portions, to reduce a separation distance between the inner surface of each of the expanded disk portions and the central portion.

2. The medical device of claim 1, wherein the central portion is cylindrical in shape.

3. The medical device of claim 1, further comprising an occluding fiber retained within at least one of the central portion or the two expanded disk portions.

4. The medical device of claim 1, further comprising means for securing one of the proximal or distal ends of the tubular metal fabric, thereby gathering the plurality of braided metal strands and inhibiting unraveling of the plurality of braided metal stands.

5. The medical device of claim 4, wherein said means for securing comprises at least one clamp at the proximal end or the distal end.

6. The medical device of claim 5, wherein the at least one clamp has a threaded bore for rotational attachment to a delivery device.

7. The medical device of claim 1, wherein the central portion is concentric with the two expanded disk portions.

8. The medical device of claim 1, wherein the first expanded disk portion is at the proximal end of the medical device, and wherein the second expanded disk portion is at the distal end of the medical device.

9. The medical device of claim 1, wherein the first and second reduced diameter portions are flexible such that the first and second expanded disk end portions are configured to pivot about the first and second reduced diameter portions, respectively.

10. The medical device of claim 1, wherein at least one of the two expanded disk portions is planar in shape.

11. The medical device of claim 1, wherein at least one of the two expanded disk portions is cupped towards the central portion and at least partially overlaps the corresponding reduced diameter portion.

12. The medical device of claim 1, wherein each of the two expanded disk portions respectively comprises the inner face, facing the central portion, and an opposing outer face, wherein the inner face of at least one of the two expanded disk portions is concave towards the central portion.

13. The medical device of claim 1, wherein each of the two expanded disk portions respectively comprises the inner face, facing the central portion, and an opposing outer face, wherein the medical device further comprises an occluding fiber within the tubular metal fabric, the occluding fiber coupled to the inner face of at least one of the two expanded disk portions.

14. The medical device of claim 13, wherein the occluding fiber is further coupled to the central portion of the medical device.

15. The medical device of claim 1, wherein a ratio of a diameter of the expanded disk portions to a diameter of the of the first and second reduced diameter portions is about 10:1 to 25:1.

16. A method for delivering a medical device of claim 1 to an opening in a body, the method comprising:
constraining the medical device to the collapsed configuration;
delivering the medical device to the opening; and
deploying the medical device in the opening such that the medical device at least partially returns to the expanded preset configuration.

17. The method of claim 16, wherein the deploying comprises:
deploying the first expanded disk portion at the distal end of the medical device to engage a distal wall at one side the opening at a first angle with respect to the opening;
deploying the central portion within the opening; and
deploying the second expanded disk portion at the proximal end of the medical device to engage a proximal wall at an opposing side of the opening at a second angle with respect to the opening.

18. The method of claim 16, wherein the deploying comprises deploying the medical device such that the two expanded disk portions assume a non-parallel relationship on opposing sides of the opening.

19. The method of claim 16, further comprising rotating a delivery device coupled to the medical device to decouple the delivery device from the medical device.

* * * * *